United States Patent
Meglin, legal representative et al.

(10) Patent No.: US 7,048,729 B2
(45) Date of Patent: May 23, 2006

(54) CATHETER AND METHOD OF FLUID REMOVAL FROM A BODY CAVITY

(76) Inventors: Allen J. Meglin, legal representative, 1912 Ashbrook Dr., Wilmington, NC (US) 28403-5302; Matthew Meglin, deceased, late of Wilmington, NC (US)

(*) Notice: Subject to any disclaimer, the term of this patent is extended or adjusted under 35 U.S.C. 154(b) by 0 days.

(21) Appl. No.: 10/172,160

(22) Filed: Jun. 14, 2002

(65) Prior Publication Data
US 2003/0191452 A1 Oct. 9, 2003

Related U.S. Application Data

(60) Provisional application No. 60/370,558, filed on Apr. 4, 2002.

(51) Int. Cl.
*A61K 9/22* (2006.01)
(52) U.S. Cl. .............. 604/890.1; 604/288.02; 604/288.04
(58) Field of Classification Search .......... 604/288.01, 604/288.02, 288.04, 288.05, 890.1, 891.1, 604/892.1
See application file for complete search history.

(56) References Cited

U.S. PATENT DOCUMENTS

| | | | | | |
|---|---|---|---|---|---|
| 3,602,228 | A | * | 8/1971 | Cowley | ............... 604/103 |
| 4,802,885 | A | * | 2/1989 | Weeks et al. | ........... 604/288.02 |
| 4,880,414 | A | | 11/1989 | Whipple | |
| 4,963,133 | A | | 10/1990 | Whipple | |
| 5,085,644 | A | * | 2/1992 | Watson et al. | ............... 604/153 |
| 5,112,303 | A | * | 5/1992 | Pudenz et al. | ............... 604/502 |
| 5,800,390 | A | * | 9/1998 | Hayakawa et al. | ....... 604/93.01 |

OTHER PUBLICATIONS

PORT-A-CATH® Peritoneal Implantable Access Systems, Instructions for Use, Deltec, SIMS Deltec, Inc., St. Paul, MN 55112 U.S.A., May 1996, pp. 1-19.
PORT-A-CATH® P.A.S. PORT® Systems, Implantable Venous Access Systems, Product Specifications, Deltec, SIMS Deltec, Inc., St. Paul, MN 55112 U.S.A., 1999, pp. 1-2.

* cited by examiner

*Primary Examiner*—Kevin C. Sirmons
(74) *Attorney, Agent, or Firm*—Lowrie, Lando & Anastasi, LLP

(57) ABSTRACT

A catheter comprises a catheter body having a wall defining a lumen therein and having plural holes defined through the wall in a pattern which prevents loculation, migration and blockage of a fluid flow through the lumen, the catheter body having a tissue-puncture resistant shape; and a port having a reservoir capable of multiple needle accesses. The catheter is useful for draining fluids from a patient's body cavity, for example the peritoneal cavity.

20 Claims, 4 Drawing Sheets

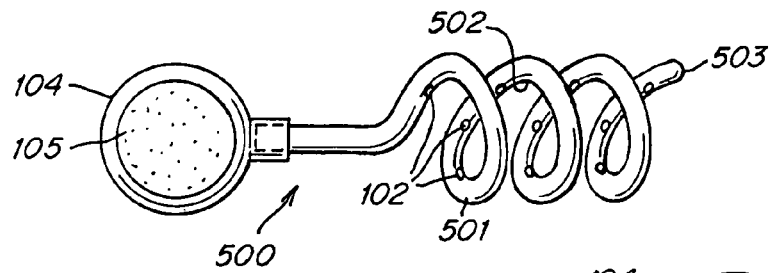
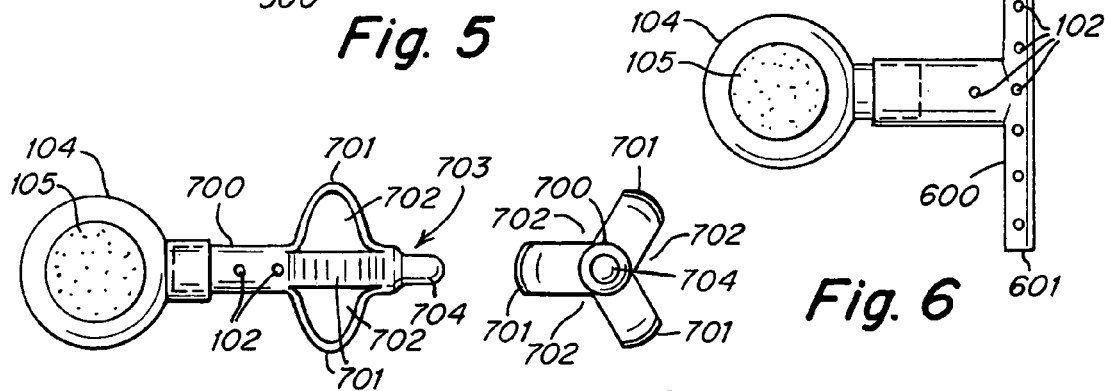
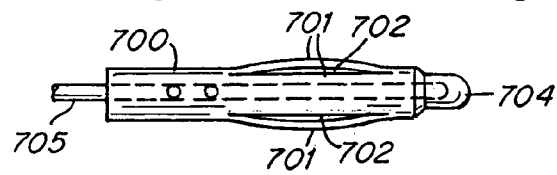
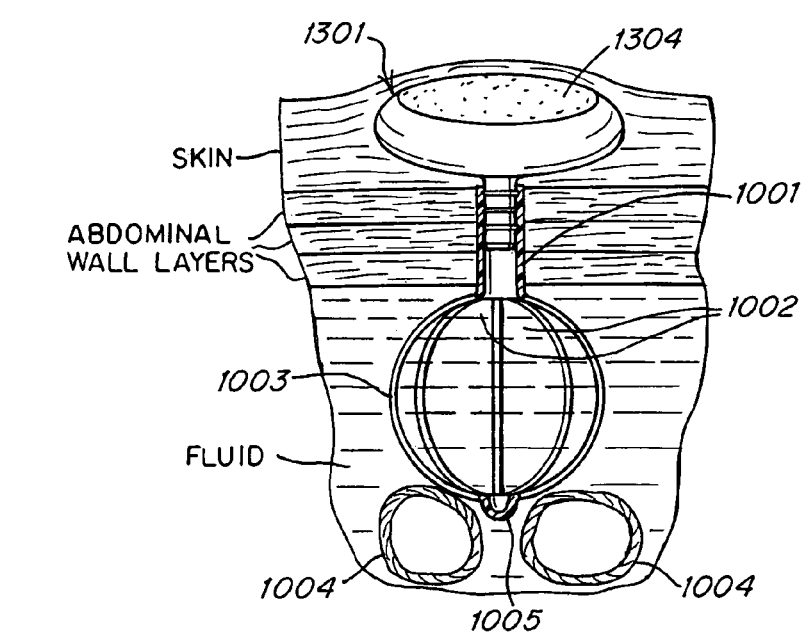

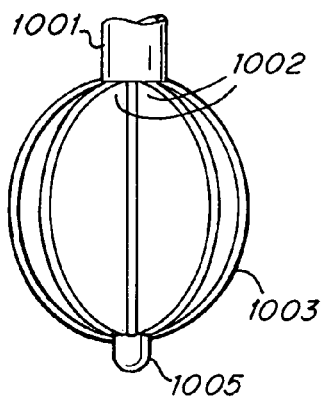 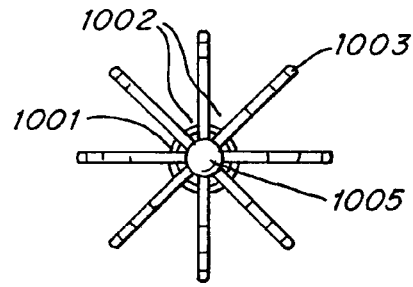
Fig. 11　　　Fig. 12
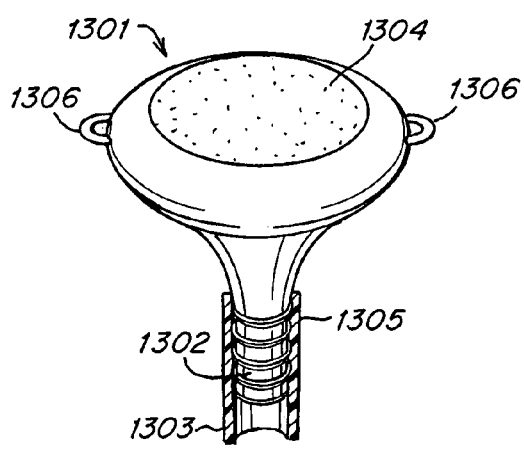 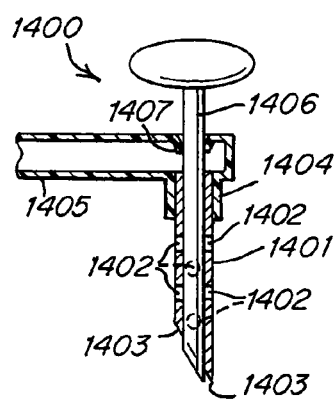
Fig. 13　　　Fig. 14
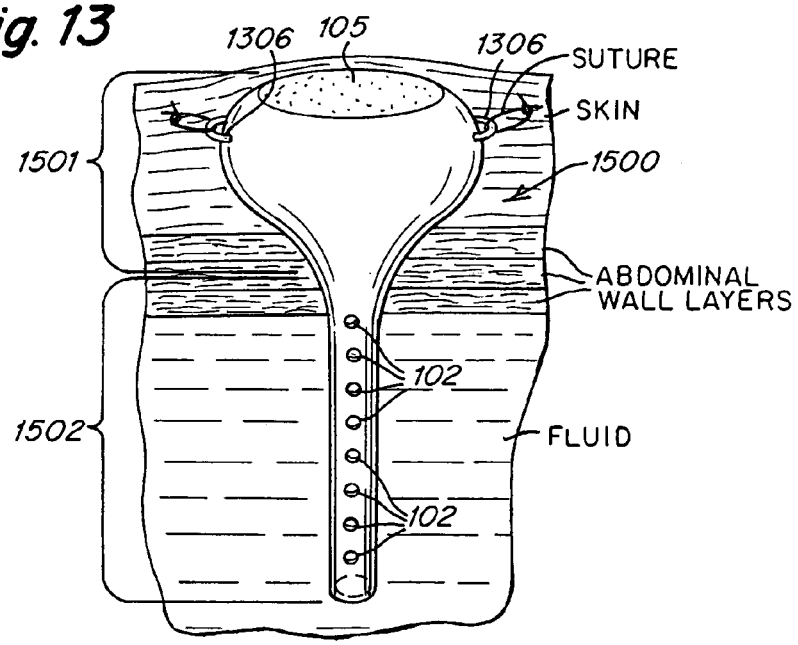
Fig. 15

US 7,048,729 B2

CATHETER AND METHOD OF FLUID REMOVAL FROM A BODY CAVITY

CROSS-REFERENCE TO RELATED APPLICATIONS

This application claims domestic priority under 35 U.S.C. §119(e) to U.S. Provisional Patent Application Ser. No. 60/370,558 filed Apr. 4, 2002, incorporated herein by reference.

This application is related to U.S. Provisional Patent Application Ser. No. 60/178,055, filed Jan. 24, 2000, incorporated herein by reference.

BACKGROUND

The present invention relates to devices that permit repeated access to the peritoneal or thoracic cavities. More particularly, the invention relates to a peritoneal and thoracic cavity port catheter.

Certain medical conditions (e.g., ovarian cancer) are treated by infusing a body cavity with a fluid medical preparation through a catheter with one or more infusion holes at a distal end thereof and with an access port or other such device at a proximal end thereof.

In the case of ovarian cancer, the radioactive isotope $P_{32}$ is administered in a fluid medium infused into the peritoneal cavity, in which the patient's ovaries are located. When ovarian cancer metastasizes or spreads from the ovaries, the cancer cells simply fall off of the ovaries and spread around the peritoneal cavity, but generally do not enter the blood stream. Therefore, a therapy, which floods the peritoneal cavity with P32, is effective, without unnecessarily exposing the patient to radioactivity in undesired areas. However, ovarian cancer cells, having somewhat defective cell membranes, leak fluids, called ascites, into the peritoneal cavity. Treatment of ovarian cancer includes removal of this fluid. The procedure for doing so typically uses the same catheter through which the infusion is performed, and takes about four hours, requiring hospitalization, and is performed about once a week.

Because conventional infusion catheters are optimized for infusion, they can only be used to remove fluids from the peritoneal cavity very slowly, resulting in the long, periodic hospitalization for ovarian cancer patients.

There are similar needs under some circumstances to have access to the thoracic cavity or other body cavities, and current devices for obtaining such are similarly limited.

SUMMARY OF THE INVENTION

In accordance with aspects of an embodiment of the invention, there may be provided a catheter, comprising a catheter body having a wall defining a lumen therein and having plural holes defined through the wall in a pattern which prevents loculation, migration and blockage of a fluid flow through the lumen, the catheter body having a tissue-puncture resistant shape; and a port having a reservoir capable of multiple needle accesses.

BRIEF DESCRIPTION OF THE DRAWINGS

In the figures, in which like reference designations indicate like elements:

FIG. 5 is a top view of an alternate catheter configuration embodying aspects of the invention;

FIG. 6 is a top view of yet another alternate catheter configuration embodying aspects of the invention;

FIG. 7 is a top view of an alternate catheter and port configuration embodying aspects of the invention;

FIG. 8 is an end view of the catheter of FIG. 7;

FIG. 9 is a top view of the catheter of FIGS. 7–8, extended by a pusher rod shown in phantom;

FIG. 10 shows a cross section of a patient's peritoneal cavity, into whose wall another configuration of port and catheter has been implanted;

FIG. 11 is a side view of the distal end of the catheter body of FIG. 10;

FIG. 12 is an end view of the catheter body of FIG. 10;

FIG. 13 is a perspective view of the port and catheter connection of the embodiment of FIG. 10;

FIG. 14 is a cross-sectional side view of a removable core access needle used in various embodiments;

FIG. 15 is a side view of a catheterless plug;

DETAILED DESCRIPTION OF EMBODIMENTS

Figure 1:
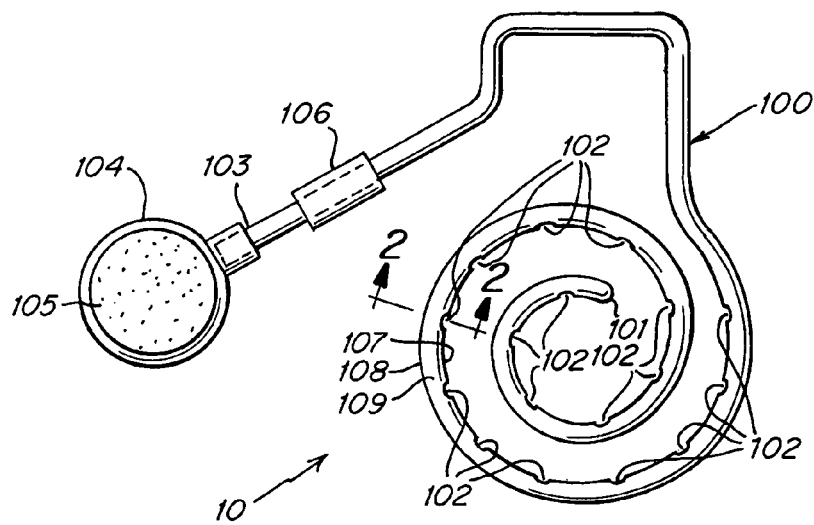
FIG. 1 is a top view of a catheter and port embodying aspects of the invention.

In accordance with some embodiments of the present invention, a method and apparatus is provided for removal of fluids from a patient's body, for example draining fluids from a body cavity between multiple drug infusion operations (e.g., during the entire duration of treatment).

Embodiments of aspects of the invention may include a catheter or a catheterless plug having a catheter body and an access port, and a method of extracting fluid from a body cavity. As explained more fully below, the catheterless plug has a body resembling a catheter body, but which can comprise a fully integrated unit. References below to the catheter body apply to the body of the catheterless plug, as well, except where differences are explicitly mentioned.

The catheter body should preferably have a shape that is unlikely to undesirably puncture or injure tissue or organs encountered in or about the body cavity to be drained. The shape of the catheter body, together with the placement of one or more fluid extraction holes in a wall of the catheter body should preferably be such as to avoid the formation of pockets (referred to by those skilled in this art as loculation) and/or to avoid creating a fluid flow that would cause migration of the catheter body, or of tissue or debris, that could block the extraction holes. For example, the extraction holes can be positioned in a protected region of the catheter body, as described below.

The catheter port should preferably be implantable subcutaneously, and/or capable of sufficient extraction needle passages to complete a course of treatment without replacement.

The invention is now illustrated in further detail with reference to some embodiments thereof. In the following description the illustrative example of extracting fluid from the peritoneal cavity is used. However, it should be understood that the invention may be employed in connection with treatments requiring the extraction of fluid from the thoracic cavity or another body cavity.

One aspect of the invention is illustrated in connection with a catheter 10 including a catheter body 100 (FIGS. 1–3) having a lumen (FIG. 2, 200) that may be closed off at the distal end 101, i.e., having no end hole. This embodiment includes plural holes 102 covering a combined surface area suitable for withdrawing fluid, substantially without clogging. Thus, when the catheter 10 is used to extract fluid from the peritoneal cavity, there is no large suction through a dominant single point which could attract occluding masses to migrate to the dominant single point or could attract the catheter itself to migrate into a position where a dominant single point is occluded. Optionally, in another embodiment, an end hole can be provided at the distal end 101 of catheter body 100, together with one or more other holes 102, provided neither a hole 102 nor the optional end hole contributes such a surface area, and consequently large fluid flow, as to induce loculation or migration of the catheter body 100.

In order to provide more room for holes 102, the catheter body 100 of this embodiment is quite long. One danger inherent in implanting a catheter 10 in many body cavities is the risk of perforating or puncturing an organ, membrane, or other tissue unintentionally. The risk is especially large when a long catheter body 100 is implanted into a closed cavity such as the peritoneal cavity, with the expectation that the catheter will bunch up like spaghetti.

Figure 2:
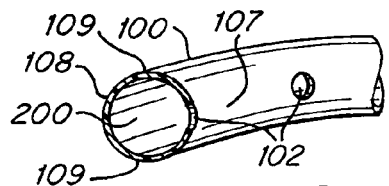
FIG. 2 is a cross sectional detail view of the catheter of FIG. 1, taken along line 2—2.
Figure 3:
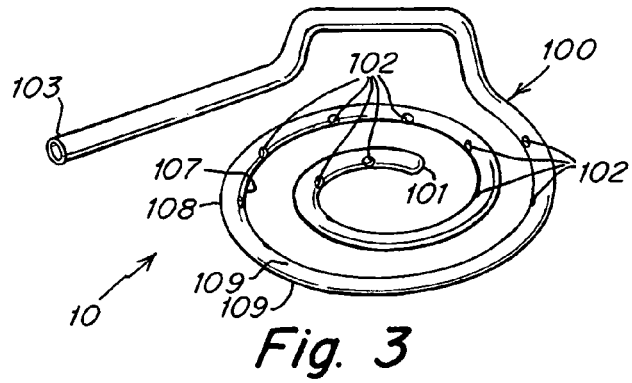
FIG. 3 is a perspective view of the catheter of FIG. 1.

In the embodiment of FIGS. 1–3, the catheter body 100 is a self-coiling type to facilitate insertion of such a relatively long catheter into the body. This may be achieved by means known to the skilled practitioner such as molding the catheter body 100 in a desired coil configuration, molding the catheter body 100 on a coiled strength member such as a wire, etc. The coil may be flat, a straight-sided helix, a conical helix, etc.

The embodiment of FIGS. 1–3 employs a flat coil pigtail configuration, although other coil configurations, as well as configurations that avoid perforation or puncture using other shapes, as explained below, are possible.

As stated above, the holes 102 should be positioned to avoid contact with adjacent tissues or occluding masses. The holes 102 of this embodiment are positioned on the inner curve 107 of the coil so as to avoid contact between the holes 102 and adjacent tissues. The outer curve 108 and the sides 109 can be devoid of holes. Thus, the holes 102 are in a protected region of the catheter body. As used herein, "inner curve" refers to that part of the surface of a coil-shaped catheter body 100 facing a central axis of the coil of the catheter body 100. Also as used herein, "outer curve" is that part of the surface of the coil-shaped catheter body 100 facing away from a central axis of the coil of the catheter body 100. Finally as used herein, "sides" are surfaces of the coil-shaped catheter body 100 adjacent to both the inner curve 107 and outer curve 108 and joining them.

As mentioned, other shapes can also avoid puncturing adjacent tissues, organs and membranes, while distributing holes 102 to prevent loculation, migration or occlusion. As shown in FIG. 5, an alternate embodiment of a catheter 500 has a catheter body 501 with a shape such as a simple helix or corkscrew, that avoids punctures. Holes 102 are disposed on the inner curve 502 of the catheter body 501 to avoid contact between the holes 102 and adjacent tissues. Again, the holes 102 are located in a protected region of the catheter body. This catheter 500 and the catheter 10 of FIGS. 1–3 can optionally include an end hole (not shown) at the distal end 503 provided the area of the end hole is properly balanced against the areas of the holes 102.

Another catheter body shape possessing desirable characteristics of avoiding punctures, loculation, migration and occlusion is shown in FIG. 6. In this example, catheter body 600 has a T-bar shape. The terminuses 601 may be closed or may optionally include end holes (not shown) at the terminuses 601.

Yet another suitable catheter body shape is shown in FIGS. 7–9. This catheter body 700 has what is referred to as a "tulip" shape. The surfaces of the tulip "petals" 701 can be opened into holes 702. The center 703 of the tulip may be a closed end nipple 704, which captures a pusher rod 705 by which the catheter body 700 is advanced during implantation. When the pusher rod 705 is extended, the end of the catheter body 700 stretches, collapsing the tulip petals 701 as shown in FIG. 9. When the pusher rod 705 is withdrawn, after implantation, the tulip petals 701 expand as shown in FIGS. 7 and 8. This configuration can be shorter then those of FIGS. 1–3 and 5–6 because the shape of petals 701 permits holes 702 to have a large surface area compared to holes 102.

Another suitable arrangement for the catheter body that prevents blockage, puncture or loculation is shown in FIGS. 10–12. This embodiment has a short body 1001 terminating in one or more fluid extraction holes 1002. The fluid extraction holes 1002 are surrounded by a spherical cage 1003 that prevents organs, e.g. the bowels 1004, or debris from blocking the extraction holes 1002. The cage 1003 may have other shapes, but a spherical cage 1003 presents no sharp edges or steps that are likely to cause problems during implantation or removal. Because the cage 1003 surrounds the fluid extraction holes 1002, the extraction holes 1002 are in a protected region of the catheter body.

The spherical cage 1003 of this embodiment can be formed of plastic, metal, or any other suitable material. If formed of plastic, the cage 1003 can be molded integrally with the body 1001 of the catheter, in the expanded spherical shape shown in FIGS. 10–12. If formed of metal, the cage 1003 can be preformed, also in the expanded spherical shape shown in FIGS. 10–12. The metal can be Nitinol or another so-called "memory metal" which can be alternately stowed or deployed, for example by alternate application of room ambient temperature and of the patient's own body heat. A metal spherical cage 1003 would also be formed integrally with and molded into the plastic of catheter body 1001. In an alternative method of stowing and deploying the device, as in the case of the tulip design described above in connection with FIGS. 7–9, the spherical shape can be collapsed by a pusher rod engaging an end tab 1005 during insertion and extraction. The pusher rod is withdrawn completely from the catheter body while the catheter is in situ in a patient's body.

The catheter body (FIG. 1, 100; FIG. 5, 501; FIG. 6, 600, FIG. 7, 700, FIG. 10, 1001) may be constructed of any suitable materials, using any suitable methods. Holes 102, 702, where applicable, may be molded into the catheter or formed by any other suitable technique, e.g., laser drilling, which can produce holes suitable for rapid fluid extraction. The size, shape and location of the holes should be selected to be suitable for fluid extraction, as explained above. However, infusion can also be performed through the holes. Without limitation, suitable materials include plastics and elastomers such as silicone, polyurethane and polyethylene and the like.

Ports usable in connection with the catheter bodies described above are now described.

In the embodiment of FIG. 1, the proximal end 103 of the catheter body 100 terminates at and is connected for fluid communication to a subcutaneously implantable port 104. The port has a membrane (referred to as a septum) 105 for percutaneous access to the port 104 by a suitably sized extraction needle, e.g., a 14-gauge needle. In one embodiment, the septum 105 is durable enough to permit at least 50 or more non-coring, self-healing passages by a 14 gauge or larger needle. In other embodiments, the septum 105 can withstand at least 100 or more, and preferably 200 or more passages.

The port 104 is constructed of any suitable materials, using any suitable methods. In one embodiment, the side walls and back wall of the port 104 may be formed of titanium, but other metals or plastics such as acetal homopolymers that are bioinert can be used, for example. The top surface is the septum 105, which may be formed of silicone or other elastomer or plastic. In embodiments capable of withstanding 200 passages by a 14-gauge needle, the septum 105 of silicone has a surface area of about 1–6 $cm^2$ and be about 2–4 mm thick. Typically, but without limitation thereto, the septum 105 may have dimensions of about 1–2 cm by 1–3 cm.

The walls and septum 105 of the port 104 define a reservoir within that has a low, wide profile to minimize the volume of fluid held in the reservoir, and to maximize the comfort to the patient in whom the port 104 is implanted. The port may, without limitation thereto, have overall dimensions of 2 cm by 4 cm by 1 cm. Such a port 104 can be implanted in a large pocket formed on the patient's abdominal wall or in another location that avoids interference with patient mobility. The catheter body 100 and port 104 may include any suitable connector feature for connecting one to the other. For example, a conventional hub connection (not shown) can be used.

Figure 4:
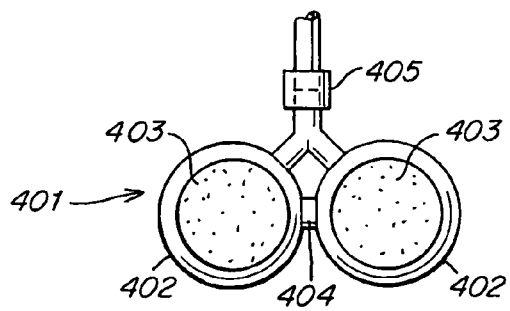
FIG. 4 is a top view of an alternate port configuration embodying aspects of the invention.

FIG. 4 shows an alternate embodiment of the invention directed to a multi-septum configuration. This multi-septum configuration is useable in combination with any of the catheter body configurations disclosed herein, and any other catheter body configurations. In the embodiment of FIG. 4, the port 401 at the proximal end 103 of the catheter 100 has two chambers 402, each have a septum 403, allowing two needles to be placed for more rapid drainage. The chambers 402 may be interconnected 404, and may be connected to a single catheter 100 through a single hub 405.

In the alternative embodiment shown in FIG. 13, the port 1301 has a ribbed outlet 1302 to which the catheter body 1303 is attached. A, ribbed outlet 1302 such as shown can be used instead of a conventional hub, such as mentioned above. In this embodiment, the port outlet 1302 is disposed opposite the septum 1304, an arrangement also thought to be advantageous in some cases.

Use of a ribbed outlet 1302 simplifies the construction and assembly of the catheter and port. The proximal end 1305 of the catheter body 1303 is simply slipped over the ribbed outlet 1302, and is held in place by friction between the catheter body 1303 and the ribbed outlet 1302.

Placing the ribbed outlet 1302 opposite the septum 1304 is advantageous at least in that the impedance of the structure to fluid flow is reduced relative to placing the outlet to the side of the port, as in the embodiments of FIGS. 1–7. Moreover, implantation can be simplified using this arrangement because the entire assembly is inserted straight into the cavity to be drained, rather than at an angle or along a convoluted path. Yet another advantage of this arrangement is that the catheter is less likely to kink than in a configuration where the catheter body has to transition from a position parallel to the abdominal wall to one perpendicular to the abdominal wall.

Figure 22:
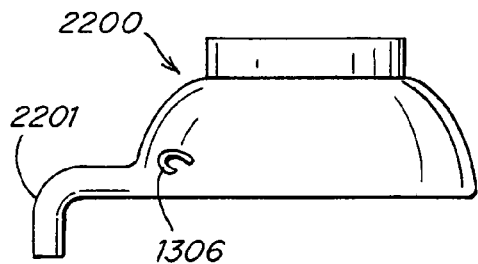
FIGS. 22 and 23 are side and top views, respectively, of a port design having a right-angle outlet.
Figure 23:
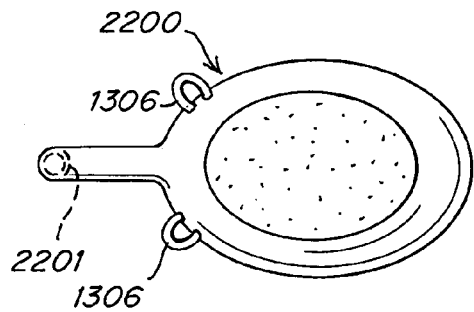

In another alternative embodiment, shown in FIGS. 22 and 23, exhibiting advantages similar to those of the embodiment of FIG. 13, a right-angle outlet 2201 is employed. Port 2200 is substantially similar in construction and arrangement to port 104 of FIG. 1. However, outlet 2201 makes a right-angle bend towards the direction of implantation of a catheter body (not shown), so that kinks or bends are not introduced into the catheter body. Outlet 2201 may terminate in a conventional hub (not shown) or ribbed section (not shown) to grip the catheter body.

The port may also include other useful features. For example, the port may include suture loops 1306 by which the port can be secured to tissue in the patient's body. The port may have funnel shape to further reduce the impedance of the assembly to fluid flow during extraction.

As identified above, the port (FIG. 1, 104) can be accessed through the septum 105 by a conventional access needle, for example a 14-gauge needle. Alternatively, a removable core access needle 1400, such as shown in FIG. 14, can be used. Such a needle may include a large bore, e.g., 14 gauge, hollow point 1401. The point 1401 may be made of metal, perforated on the sides thereof 1402, and have a beveled entry edge 1403 to prevent occlusion while in use. The point 1401 is affixed to a right-angle end 1404 of a suitable type of tubing 1405 that resists collapse under suction. In order to control access through such a needle, and to prevent coring of the septum (FIG. 1, 105) during insertion, the removable core access needle 1400 has a removable stylete 1406 that resides within the hollow of the point 1401 when not accessing the port, and that is withdrawn when accessing the port. Stylete 1406 removal is facilitated by providing a diaphragm or septum 1407, through which the stylete 1406 passes and may be inserted or withdrawn.

It has been found that no cuff, as is often conventionally provided, is necessary. However, if desired, a bacteriostatic cuff 106 may provided near the proximal end 103 of the catheter body 100, so as to prevent inward migration of an infection. The cuff 106 promotes fibrous tissue ingrowth. Bacteriostatic cuffs of polyester impregnated with bacteriostatic compounds are suitable.

Leaking around the catheter can be prevented by use of a tissue collagen injection at one or more sites around the implanted system. Tissue collagen acts as a kind of biocompatible glue between the catheter body 100 and port 104, and the surrounding tissues.

In yet another embodiment, a fully integrated, catheterless fluid extraction plug 1500 is shown in FIG. 15. This embodiment combines several features described above in connection with other embodiments, as now described.

The exemplary catheterless drainage plug 1500 has an expanded port section 1501 and an elongated body section 1502. Any suitable port section shape can be used in combination with any suitable body section shape, including those shown in the other exemplary embodiments.

The catheterless plug embodiment is advantageous because of its simplicity. Without joints and rough edges that may be found in other designs, there are fewer locations to harbor potentially infectious matter or irritate the implantation site in the patient. The device is also less expensive and easier to manufacture than designs using multiple components and joints.

The devices described herein are all implanted using suitable techniques, including techniques known in the art. One such technique is now described.

First an incision is made in the patient's skin above the location where the device is to be implanted. The incision exposes a small area of the underlying cavity wall. A hollow needle is inserted through the cavity wall until a "fluid flash" is seen, that is an outflow of fluid from within the body cavity. The fluid flash indicates that the needle has been inserted into the desired location. Next, a guide wire is inserted through the needle to provide a defined path for the remainder of the devices employed. The needle is then withdrawn over the guide wire. A sheath and dilator are next inserted, over the guide wire. The dilator enlarges the hole through the cavity wall sufficiently to allow a catheter to be inserted. After the dilator has enlarged the hole, it is removed. The catheter is then slid over the wire and sheath and through the enlarged hole. Finally the sheath, and optionally the wire, is withdrawn, leaving the catheter in place.

Figure 16:
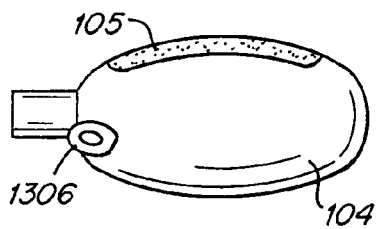
FIGS. 16, 17 and 18 are side, top and front views, respectively, of an alternate port design.
Figure 17:
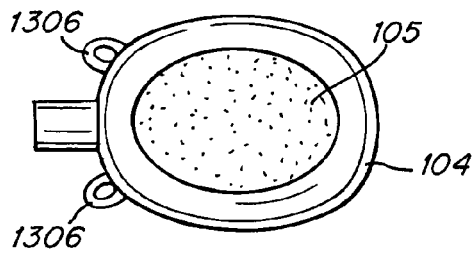
Figure 18:
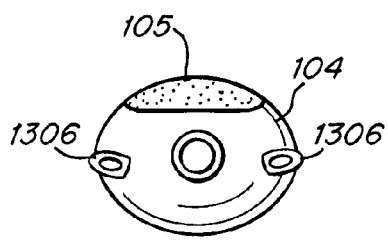

Various modifications to the port could now be evident to the skilled artisan. For example, the bottom of the port could be curved to follow the curve of the patient's abdomen, for patient comfort. Alternatively, the port could be "almond-"shaped to leave room for two extraction needles. Preferably, the port shape accommodates a septum large enough to permit rotation of the skin/septum puncture site, so as to avoid skin breakdown as a result of repeated needle punctures. See, for example, FIGS. 16–18. The almond shape would allow room for deep needles, for example needles including side holes. Hollow needles with side holes would permit higher extraction flow rates than hollow needles having only an end hole. The eyelets 1306 may be filled with a membrane or not, as desired.

Figure 19:
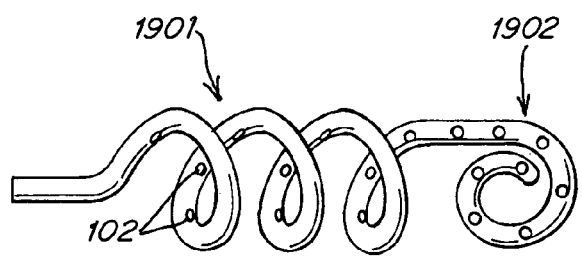
FIG. 19 is a side view of a combined catheter shape.
Figure 20:
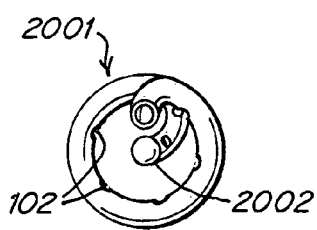
FIGS. 20 and 21 are end and side views, respectively, of an alternate combined catheter shape.
Figure 21:
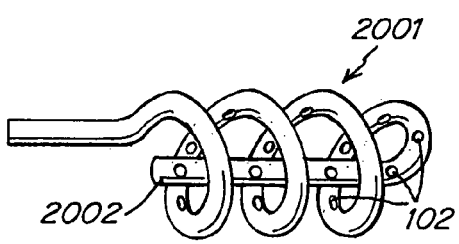

According to yet other variations, the shapes and features described above, and others, can be combined, as for example as shown in FIGS. 19–21. FIG. 19 shows a helix 1901 combined with a pigtail 1902. FIGS. 20 and 21 show a helix 2001 combined with a straight section 2002. In each case, the geometry is such that it allows straightening followed by self-coiling or bunching, for implantation.

The present invention has now been described in connection with a number of specific embodiments thereof. However, numerous modifications, which are contemplated as falling within the scope of the present invention, should now be apparent to those skilled in the art. Therefore, it is intended that the scope of the present invention be limited only by the scope of the claims appended hereto.

What is claimed is:

1. A catheter for removing fluid from a body cavity, comprising:
    a catheter body having a wall defining a lumen therein and having at least one hole defined in the catheter body in a location that is within a body cavity when implanted, and which in combination with a shape of the catheter body prevents loculation, migration and blockage of a fluid flow through the lumen when the fluid flow is induced from a distal end to a proximal end thereof, the catheter body having a tissue-puncture resistant shape; and
    a port having on one surface a septum capable of multiple needle accesses; wherein
    the distal end of the catheter body has an expanded, blunt shape including a cage structure enclosing the at least one hole; wherein
    the cage is collapsible when advanced by a pusher rod; and
    wherein the cage structure is composed essentially of a plastic material.

2. The catheter of claim 1, wherein the septum has sufficient surface area and thickness to sustain over 50 passages by an 18 gauge needle.

3. The catheter of claim 2, wherein the septum has sufficient surface area and thickness to sustain over 100 passages by the 18 gauge needle.

4. The catheter of claim 3, wherein the septum has sufficient surface area and thickness to sustain over 200 passages by the 18 gauge needle.

5. The catheter of claim 1, further comprising:
    another port coupled to the first port and to the body of the catheter for fluid communication therewith.

6. The catheter of claim 1, wherein the port has an outlet that terminates opposite the port from the septum.

7. The catheter of claim 6, wherein the outlet exits the port from a surface opposite the septum.

8. The catheter of claim 6, wherein the outlet exits the port from a side of the port and makes a right-angle bend.

9. The catheter of claim 1, wherein the distal end of the catheter body has an expanded, blunt shape including a cage structure enclosing the at least one hole; and the distal end further comprising:
    wherein the cage structure is composed essentially of a memory metal having an expanded shape at about a patient's body temperature and a collapsed shape at another temperature.

10. The catheter of claim 1, wherein the cage is an integral part of the catheter body.

11. The catheter of claim 10, wherein the cage is retained as an integral part of the catheter body by a portion of the catheter body overmolded onto the cage.

12. The catheter of claim 1, wherein the catheter body is connected to the port at a location substantially opposite the one surface on which the port has the septum, so that implantation can be performed substantially straight into a body cavity to be drained.

13. The catheter of claim 1, which when implanted positions the septum substantially parallel to the epidermis under which it is implanted and the catheter body extends from the port without bends and in a direction substantially perpendicular to the epidermis into a body cavity to be drained.

14. The catheter of claim 13, wherein the catheter body has a short length, such that the catheter body is substantially immobilized in a wall of the body cavity and fluid flow into the lumen through the at least one hole produces a force primarily in a direction perpendicular to the wall of the body cavity, thus preventing loculation and migration.

15. A catheter for removing fluid from a body cavity, comprising:
    a catheter body having a wall defining a lumen therein and having at least one hole defined in the catheter body in a location that is within a body cavity when implanted, and which in combination with a shape of the catheter body prevents loculation, migration and blockage of a fluid flow through the lumen when the fluid flow is induced from a distal end to a proximal end thereof, the catheter body having a tissue-puncture resistant shape; and
    a port having on one surface a septum capable of multiple needle accesses, which when implanted positions the septum substantially parallel to the epidermis under which it is implanted and the catheter body extends from the port without bends and in a direction substantially perpendicular to the epidermis into a body cavity to be drained, the distal end defined by a flexible, openwork cage structure.

16. The catheter of claim 15, wherein the cage structure defines openings though which fluid freely passes while the cage structure prevents inward migration of objects in the body cavity toward the at least one hole.

17. The catheter of claim 15, the cage collapsible when advanced by a pusher rod.

18. The catheter of claim 15, wherein the cage structure includes a memory metal structure having an expanded shape at about a patient's body temperature and a collapsed shape at another temperature.

19. The catheter of claim 15, wherein the cage is molded integrally with the catheter body.

20. The catheter of claim 19, wherein the cage is retained in the catheter body by a portion of the catheter body overmolded onto the cage.

* * * * *

UNITED STATES PATENT AND TRADEMARK OFFICE
CERTIFICATE OF CORRECTION

PATENT NO. : 7,048,729 B2
APPLICATION NO. : 10/172160
DATED : May 23, 2006
INVENTOR(S) : Allen J. Meglin et al.

It is certified that error appears in the above-identified patent and that said Letters Patent is hereby corrected as shown below:

In Section (76), on the Title page, the Inventor section, should read:

Inventors: "Allen J. Meglin, Wilmington, NC (US); and Allen J. Meglin, legal representative, 1912 Ashbrook Dr., Wilmington, NC (US) 28403-5302: Mathew Meglin, deceased, late of Wilmington, NC (US)"

Signed and Sealed this

Twenty-ninth Day of August, 2006

JON W. DUDAS
*Director of the United States Patent and Trademark Office*